United States Patent [19]  [11] Patent Number: 4,897,267
Bontemps et al.  [45] Date of Patent: Jan. 30, 1990

[54] MICROPARTICLES COMPRISING A BIODEGRADABLE POLYMER CONTROLLING THE RELEASE OF AN ANTIMALARIA ACTIVE PRINCIPLE, PHARMACEUTICAL COMPOSITIONS COMPRISING IT AND PROCESS FOR ITS PREPARATION

[75] Inventors: José Bontemps, Xhendremael; Philippe Pirson, Wezembeek-Oppem; Jean-Bernard Falmagne, Wavre; Robert Jerome, Tilff; Philippe Teyssie, Condroz; Luc Delattre, Oupeye; Brigitte Evrard, Verlaine, all of Belgium

[73] Assignee: Ire-Celltarg S.A., Fleurus, Belgium

[21] Appl. No.: 225,395

[22] Filed: Jul. 28, 1988

[30] Foreign Application Priority Data

Jul. 30, 1987 [FR] France ............................ 87 10802

[51] Int. Cl.$^4$ ............................................. A61F 13/00
[52] U.S. Cl. .................................... 424/422; 424/423; 424/426; 424/486; 424/489
[58] Field of Search ................ 514/895; 424/422, 423, 424/426, 489, 486

[56] References Cited

U.S. PATENT DOCUMENTS 3,082,154  3/1963  Allan ................................ 514/895 X
3,663,552  5/1972  Yardley et al. ................... 514/895 X
4,284,627  8/1981  Raether et al. .................. 514/895 X
4,416,872  11/1983 Alving et al. ..................... 514/895 X

FOREIGN PATENT DOCUMENTS 0134318  3/1985  European Pat. Off. .
1945660  3/1971  Fed. Rep. of Germany ... 514/895 X
2070153  9/1971  France .

OTHER PUBLICATIONS

Chemical Abstracts, vol. 85, No. 24, 12/76, p. 315, resume #182354d, D. L. Wise et al., "Sustained Release of an Antimalarial Drug Using a Copolymer of Glycolic/-Lactic Acid", & Life Sci., 1976, 19(6), 867–73.
Chemical Abstracts, vol. 107, No. 2, 7/87, p. 349, resume #12756s, T. Laakso et al., "Biodegradable Microspheres Bound Antiparasitic Drugs from Starch Microparticles", & J. Pharm. Sci., 1987, 76(2), 134–40.
Journal of Pharmaceutical Sciences, vol. 73, No. 12, 12/84, pp. 1721–1724, American Pharmaceutical Association, S. Benita et al., "Characterization of Drug–Loaded Poly(d,1–Lactide) Microspheres".

Primary Examiner—Thurman K. Page
Attorney, Agent, or Firm—Fleit, Jacobson, Cohn, Price, Holman & Stern

[57] ABSTRACT

The present invention relates to microparticles containing an active principle against malaria, such as primaquine, one of its amino acid derivatives, or their conjugates with a hepatotropic vector or their pharmaceutically acceptable salts, and a biocompatible and biodegradable polymer controlling the kinetics of release of the active principle, like (DL)polylactide. The invention also relates to pharmaceutical compositions comprising microcapsules according to the invention. Lastly, the invention relates to processes for the preparation of microparticles as mentioned above, the processes comprising: dissolving the polymer in a volatile solvent, adding to this solution the active principle and possibly a substance regulating the size of the microparticles, and at the end of evaporation, recovering the microparticles by centrifugation and filtration.

20 Claims, No Drawings

MICROPARTICLES COMPRISING A BIODEGRADABLE POLYMER CONTROLLING THE RELEASE OF AN ANTIMALARIA ACTIVE PRINCIPLE, PHARMACEUTICAL COMPOSITIONS COMPRISING IT AND PROCESS FOR ITS PREPARATION

BACKGROUND OF THE INVENTION

Modern chemotherapy seeks to reduce the toxicity, to prolong the duration of action and to increase the selectivity of many medicaments, that is to say generally to increase the therapeutic index of the active principles. To achieve these objectives, recourse is had particularly to the use of polymeric materials controlling the release of the active principle.

At the present time there exist polymeric materials capable of ensuring control of the speed of release and the duration of action of medicaments. These systems were developed initially for contraception with steroid hormones. They are, until now, used for a wide range of active principles, both micro- and macromolecular types.

More precisely, the present invention relates to the incorporation of antimalaria agents in polymeric biomaterials by microencapsulation.

Microencapsulation groups all of the techniques enabling the obtaining of individualized particles whose size ranges between 1 and 1250 μm.

The microparticles so obtained may be divided into two groups:

microcapsules, spherical particles constituted by a solid jacket containing a liquid, solid or pasty substance. Each microcapsule constitutes a reservoir system proper;

microspheres, particles, also spherical but constituted by a continuous network of support material in which the substance to be encapsulated is dispersed, in the molecular or particulate state. This structure, homogeneous or heterogeneous as the case may be, constitute a matrix system.

Antimalarial agents concerned by the present invention have been described in patent applications FR 87 04079 and BE 200041. They are primaquine and its derivatives such as amino acid-primaquine derivatives, targeted macromolecular conjugates, such as primaquine bonded to galactosylated albumin through a tetrapeptide arm which permits the release of an active form of primaquine at the level of the lysosomes of the targeted cells. These antimalarial agents seek to combat the hepatocyte forms of malaria.

A difficulty of the inventions in the field which interests us is the need to determine the polymers having properties defined according to the type of active principle to be incorporated. It is appropriate also to determine for a given drug type the speed of release and the charge ratio ensuring optimum therapeutic coverage for a selected period.

In the same way, the technique of incorporation depends on the polymer-medicament couple particularly the existence of a solvent common to the partners, the existence of thermal properties of the latter, their miscibility, etc. In addition, this incorporation must not alter the properties of the active principle.

There exist a wide variety of monomers which can be polymerized by different methods to form macromolecular chains. By modifying the nature of the polymers and their mode of linkage, macromolecular chemistry can hence create a wide range of materials. In a biomedical context, it is crucial for the polymers used to be biocompatible, hemocompatible and/or biodegradable, the choice of polymers being also in part dictated by the way of administration.

Considering that malaria is localized in underdeveloped countries where the facilities, both medical and paramedical, are extremely limited, it is appropriate to envisage the development of an injectable galenic form whose administration is the simplest.

One of the objects of the present invention is therefore the production of injectable microparticulate forms enabling the release kinetics to be modulated by means of polymeric materials for a series of molecules active against malaria.

Medicaments absorbed orally (pills, tablets, microparticles in a capsule, etc.) may be coated by a non-biodegradable filmogenic polymer, since it will be eliminated through the tractus after being released at the level of the stomach or at the entry of the intestine. On the other hand, if injectable forms are envisaged, the polymers must show particular properties, especially of biodegradability.

GENERAL DESCRIPTION OF THE INVENTION

It is therefore an object of the present invention to provide microparticles containing a principle active against malaria, such as primaquine, one of its derivatives or their conjugates with a hepatotropic vector or their pharmaceutically acceptable salts, and a biocompatible and biodegradable polymer controlling the release kinetics of the active principle.

Primaquine derivatives incorporated according to the invention are shown diagrammatically by the formula PQ—X, in which PQ represents primaquine, X represents an amino acid or a peptide of 2 to 4 amino acids, the linkage PQ—X being a covalent peptide linkage between the free amine group of PQ and the carboxylic group of X.

The basic products PQ as well as derivatives such as PQ—X may be in the form of their addition salts with acids.

The preparation of these PQ—X derivatives has been described by Applicants particularly in patent application FR 8 704 079.

According to a particular embodiment of the process, a start is made from a salt, for example, the diphosphate of primaquine and the amino acid or peptide whose amino function is protected, for example, by a terbutyloxycarbonyl group and the following steps are carried out.

(a) N-hydroxysuccinimide or any other group activating the acid function of the amino acid or peptide is reacted with the protected derivative of the amino acid or peptide, for example, on the N-terbutyloxycarbonyl derivative of the amino acid or peptide, (b) primaquine, liberated from its salt, for example, by an ammonia solution, is reacted therefore with, for example, N-hydroxysuccinimide ester of the protected derivative of the amino acid or peptide, (c) the crude product so obtained is purified by chromatography on silica gel, (d) the protective group, such as the terbutyloxycarbonyl of the compound obtained is then cleaved in the presence of acid, for example trifluoroacetic acid to give the derivative PQ-X in salt form, for example, trifluoroacetate.

The primaquine acts as an oxidizing agent and destabilizes the membrane of the red blood cells causing hemolysis which is at the origin of its principal toxicity. The addition of an amino acid or of a peptide reduces the penetration of the primaquine into the red blood cells on account of steric hindrance.

In addition, the activity of these novel derivatives appears to be much more considerable.

Of very particular interest are the PQ—X derivatives in which X represents an amino acid or a depeptide.

Among these amino acids, may be mentioned particularly L-leucine, D-leucine, L-alanine, D-alanine, L-isoleucine, L-phenylalanine, L-glutamic acid, L-lysine, L-tyrosine and L-glutamine.

Among the particularly interesting peptides, may be mentioned the dipeptides L-alanyl-L-leucyl, L-leucyl-L-alanyl, but also the tetrapeptides (L-analyl-L-leucyl)$_2$, (L-alanyl)$_3$ L-leucyl, L-alanyl-L-leucylglycyl-L-leucyl, glycyl-L-leucyl-glycyl-L-leucyl. The conjugates with a hepatotropic vector may be, for example, targeted macromolecular conjugates of primaquine bonded to galactosylated albumin through a tetrapeptide arm described in BE 200041, but advantageously the hepatotropic vector will have a low molecular weight and will be synthetic.

More particularly, the microparticles according to the invention are microspheres constituted by a matrix of polymers within which the antimalarial active principle is distributed.

In one particular embodiment of the invention, the polymer is polylactide.

Completely atoxic, since they are metabolized into lactic acid, the polyactide polymers are characterized by a biodegradability whose degradation kinetics are particularly convenient to control the release of primaquine and its derivatives. On the other hand, polyglycolides, for example, although also biodegradable, show a too rapid speed of biodegradation for this type of active principle and polycaprolactones show a too slow speed of degradation for the type of use envisaged for the present invention.

Polylactide is preferably in (DL) form.

The molecular weight of the polymer is advantageously comprised between 10,000 and 200,000, preferably between 50,000 and 100,000.

The ratio by weight of active principle/polymer is advantageously comprised between 1 and 50% and preferably between 15 and 25%.

In a preferred embodiment of the invention, the microparticles are formulated in an injectable solution. To do this, the microparticles must have a size comprised between 1 and 250 μm, preferably comprised between 100 and 200 μm.

It is also an object of the present invention to provide pharmaceutical compositions containing such microparticles, particularly injectable pharmaceutical compositions.

It is another object of the present invention to provide a process for the preparation of these microparticles according to which:

a polymer is dissolved in a volatile solvent, to this solution the active principle and possibly a substance regulating the size of the microparticles is added, this phase is then emulsified in a dispersing non-miscible medium, the solvent is evaporated with stirring, after evaporation, microparticles are recovered by centrifugation and filtration.

The primaquine and its derivatives being water soluble, in a particular embodiment of the process according to the invention, the primaquine or one of its pharmaceutically acceptable salts is incorporated in polyactide, the solvent being acetone, the dispersant non-miscible medium being a mineral oil, such as paraffin, the substance regulating the size of the particles being a non-ionic surface-active agent.

The (DL) form of the polyactide which is most soluble in acetone is very suitable for this type of process.

The ratio by weight polymer/solvent is advantageously from 10 to 30%, preferably from 15 to 20%.

Preferably, the emulsification is done with vigorous stirring. In this way, it is possible to obtain microparticles of size less than 200 μm such as preferred to render these microparticles injectable.

As non-ionic surface-active agents may be mentioned as particularly suitable, sorbitan esters particularly sorbitan monooleate, in a concentration comprised between 1 and 10% with respect to the weight of the solvent.

These characteristics are also important in order to obtain microparticles of suitable shape and size.

Other features and advantages of the present invention will appear from the description which follows.

DESCRIPTION OF PREFERRED EMBODIMENTS

This description refers to Tables 1 to 4 which show the particle size distribution of microspheres prepared according to the invention, the in vitro release kinetics of microspheres of diameter comprised between 160 and 200 μm, and the therapeutic activity of the latter.

EXAMPLE 1

Preparation of microspheres of primaquine diphosphate incorporated in (DL) polylactide 2.7 g of (DL) polylactide is dissolved in 21 cm$^3$ of acetone with magnetic stirring overnight (16% of polymer with respect to the weight of acetone). Sorbitan monooleate (span 80) is added in an amount of 0.83 g (5% with respect to the weight of acetone). Then 0.7 g of primaquine diphosphate is added. This amount represents 25% with respect to the weight of polymer. The dispersion of this powder in the acetone solution of polymer follows, and cooling to 0° C. by the action of ultrasound.

After dissolving of the polymer and the dispersion of the active principle by ultrasound, emulsification follows immediately. The latter is done at 0° C. with mechanical stirring (motor with a 4-bladed spindle rotating at 800 rpm whilst pouring the acetone suspension slowly into 100 cm$^3$ of liquid paraffin contained in a 250 ml beaker dipping into melting ice. Then the evaporation step of the solvent takes place. The beaker is then covered by a glass plate pierced with two orifices: one to permit the passage of the stirring rod, the other to a connection to a nitrogen bomb. Mechanical stirring is then reduced to 700 rpm until the end of the preparation. It is by progressively raising the temperature of the outer bath that the solvent is evaporated to pass from an emulsion to a microparticle suspension, this operation being carried out under a slight flow of nitrogen in two phases:

slow evaporation at 0° C., for three hours, and then at 15° C. for 15 hours;

rapid evaporation; then the temperature is raised in steps of 5° C. (for 15 mins to 15° and 20° C., for 30 mins to 25°, 30° and 35° C. and for 75 mins to 40° C.)

Then on the recovery of the microspheres by centrifuging for 10 mins, then by filtering and washing with heptane which is a non-solvent for the two constituents. Then drying takes place in a vacuum oven followed by sifting.

A rapid evaporation of the acetone at a temperature of 35° C. working in an "open" beaker results in the formation of hollow or even exploded microspheres, this is why the speed of the evaporation of the acetone has been reduced. Spherical and solid microparticles are thus obtained.

So as to reduce the size of the microspheres prepared in the acetone-paraffin system with sorbitan esters, the amount of surface-active agent must be comprised between 1 and 10% with respect to the weight of the acetone and preferably 5% with span 80.

Tests were carried out by using different surface active agents at different concentrations. The surface-active agents used were the following: aluminum tristearate, and various sorbitan esters and particularly:
span 85 (sorbitan trioleate HLB=1.8)
arlacel 83 (sorbitan sesquioleate HLB=3.7)
span 80 (sorbitan monooleate HLB=4.3)
span 60 (sorbitan monostearate HLB=4.7)
These sorbitan esters were selected as a function of the hydrophile-lipophile balance of their molecules (HLB). An HLB of low value therefore will characterize a product which is more lipophile than hydrophile.

It appears that microspheres of smallest average size are obtained with 5% span 80. However, particles of smaller sizes are obtained with other sorbitan esters than with aluminum tristearate.

The conditions of emulsification are also extremely critical. Subjecting the system to mechanical stirring of 800 rpm during the addition, the average size of the microspheres is considerably reduced. In this way it is possible to obtain a considerable proportion of microspheres of size less than 200 μm (Table 1). For the in vitro and in vivo studies, the granulometric fraction comprised between 160 and 200 μm was used.

The loading ratio, ie. the ratio of incorporation of primaquine in the microspheres, is proportional to the size of the microspheres. For microspheres of size comprised between 160 and 200 μm, loading ratios of active principle of the order of 15% are obtained.

In the present application, the "loading ratio" is signified by L.R.: (weight of active principle)/(weight of microspheres).

The suspending of the primaquine phosphate in the acetone solution of polymer is not easy, the active principle agglomerating in the form of lumps difficult to disperse. It is important to use the active principle in finest granulometric form. Satisfactory results have been obtained by the dispersion of the powder with ultrasound, at the power of 100 watts for some minutes.

Regarding polymers, tests have been performed with (DL) polylactide of average molecular weights by number and by weight of the order of 55,000 and 100,000 respectively, (determined by gel permeation chromatography with polystyrene standards).

TABLE 1

Granulometric distribution (%) of four (DL) polylactide microspheres preparations containing primaquine diphosphate.

| Sample | Diameter of the microparticles (μm) | | | | | |
| --- | --- | --- | --- | --- | --- | --- |
| | 70–100 | 100–160 | 160–200 | 200–250 | 250–315 | >315 |
| ST 11 | 0.1 | 5.1 | 17.9 | 50.0 | 23.6 | 3.3 |
| ST 12 | 3.3 | 45.1 | 39.8 | 10.0 | 1.4 | 0.2 |
| ST 71 | 0.3 | 7.5 | 24.0 | 47.8 | 18.6 | 1.8 |
| ST 81 | 1.2 | 43.1 | 41.8 | 11.0 | 2.1 | 0.7 |

EXAMPLE 2

In Vitro Release Kinetics of Microspheres Prepared by the Method Described in Example 1

For the various samples taken up in Table 1, there was isolated by mechanical sifting, the granulometric fraction comprised between 160 and 200 μm, its loading ratio determined (colorimetric assay of the primaquine extracted in aqueous phase after dissolving microspheres with dichloromethane) and the release of the active principle followed for 16 days. In practice, 10–20 mg of microspheres were used for 50 ml of isotonic phosphate buffer and at pH 7.4. This suspension is stirred in a bath oscillating at 37° C. After 1 hour (mass release or "burst effect", and daily, the absorbance of the medium is measured at 259 nm after decantation of the microspheres. The results taken up in Table 2 show that these microspheres show no or little (4–5%), mass release or "burst effect", and are characterized by a kinetics of order zero over some 12 days, with a daily release speed comprised between 7.7 and 11.1%.

TABLE 2

Load ratio and kinetics of release in vitro of the granulometric fractions 160–200 μm.

| Sample | Loading ratio (%) | Amount released after 1 hour (%) | Average release speed (% day) |
| --- | --- | --- | --- |
| ST 11 | 15.0 | 0 | 8.0 |
| ST 12 | 14.5 | 0 | 11.1 |
| ST 71 | 16.1 | 4.2 | 7.7 |
| ST 81 | 17.9 | 4.8 | 8.6 |

EXAMPLE 3

Preventive Prophylactic Activity of Primaquine Diphosphate (Pq) Incorporated in (DL) Polyactide Microspheres of Size Comprised between 160 and 200 μm Experiments were done with primaquine incorporated in a biodegradable polymer, (DL) polyactide with a molecular weight of the order of 55,000, in microsphere galenic form.

The preventive activity of the primaquine thus incorporated was determined in the experimental model of murine malaria (*Plasmodium berghei*, ANKA strain, female OF1 swiss mice). The microspheres of granulometric size comprised between 160 and 200 μm were administered intramuscularly, 3 to 17 days before the infection of the mice with *P. berghei* sporozoites.

As described in Example 2, the microsphere preparations of (DL) polyactide containing primaquine, had a smaller burst effect and regular release comprised between 9 and 14 days. The therapeutic programme (injected doses, periods of coverage) was selected on the basis of daily average release characteristic of each of the preparations ST11 (8% of Pq), ST12 (11.1% of Pq) and ST17 (7.7% of Pq).

The results obtained are presented in Table 3. It is seen from this study that:

1. The daily concentration of Pq necessary to obtain complete protection of the infected animals is about 50 mg Pq/kg although the release in the animal is similar to the in vitro release.

2. The optimal period of coverage is, in the model of murine malaria, 14 days.

Thus, for the saample ST11, the partial protection is obtained at the dosage of 450 mg Pq/mg namely 36 mg/kg/day and complete protection of the infected animals at the dose of 625 mg Pq/kg namely 50 mg Pq/kg/day. In the case of the sample ST71, the dose of 700 mg Pq/kg (50 mg Pq/kg/day) is completely curative at 14 days but is no more than partly active at 17 days.

TABLE 3

Preventive prophylactic activity of primaquine diphosphate incorporated in (DL) polylactide microspheres.

| Specimen | Loading ratio (%) | Dose[a] (mg/kg) | Treatment[b] (days) | LTS/N | LTS[c] (%) |
|---|---|---|---|---|---|
| ST 11 | 15 | 450 | −7 | 3/5 | 60 |
|  |  | 625 | −7 | 5/5 | 100 |
| ST 12 | 14.5 | 450 | −3 | 5/5 | 100 |
|  |  | 450 | −7 | 5/5 | 100 |
| ST 71 | 16.1 | 700 | −10 | 5/5 | 100 |
|  |  | 700 | −14 | 5/5 | 100 |
|  |  | 700 | −17 | 3/5 | 60 |

[a]The microspheres of granulometric size comprised between 160 and 200 μm are injected in 812 miglyol solution (viscosified with 4% Thixcin R) intramuscularly. The concentrations are expressed in mg of primaquine diphosphate/kg.
[b]The treated animals are infected with P. berghei sporazoites, 3 to 17 days after the treatment.
[c]Preventive prophylactic activity (%) = the number of animals protected to the number of animals treated and infected (expressed as %).

EXAMPLE 4

Preparation of Microspheres of L-glutamylprimaquine incorporated in (DL) polylactide (A) SYNTHESIS OF AMINOACYLATED DERIVATIVES OF PRIMAQUINE:

The aminoacylated derivatives of primaquine are obtained in two steps starting from primaquine diphosphate and from the amino acid whose amino function is protected by an N-terbutyloxycarbonyl (N-TBoc) group. The first step comprises the reaction of the primaquine base with the N-hydroxysuccinimide ester o the N-TBoc derivative of the amino acid.

The crude product thus obtained is then purified by chromatography on silicagel. The product obtained in the form of a solid ± crystalline fairly hydroscopic was isolated with good yields (±70%).

The TBoc is then cleaved in the presence of trifluoroacetic acid. The aminoacylated derivative of primaquine is obtained in the form of trifluoroacetate (probably a ditrifluoroacetate salt).

In the case where subsequent purification is necessary, a reverse phase chromatography column is used and the product is eluted with the mixture acetonitrile/H$_2$O.

The aminoacylated derivative of primaquine in its free base form may be obtained by neutralising the aqueous solution containing the trifluoroacetate salt of aminoacyl-Pq with NH$_4$OH up to pH ±8 followed by vigorous extraction with dichloromethane. After evaporation of the CH$_2$Cl$_2$, there is obtained a greenish oil very difficult to handle which may be purified subsequently by chromatography on a silicagel column eluted with a mixture CH$_2$Cl$_2$—EtOH—NH$_4$OH (120-20-1).

In the method of purification of the aminoacylated derivatives of primaquine in their trifluoroacetate form using the technique of chromatography on a reverse phase column, the column used is a Merck lobar 8 column. The support is a silica bonded with C$_8$ residues. In order to avoid an oxidation process of the derivatives upon the column, elution solvents are carefully degasified. For the same reason, it is possible to envisage other types of bonded silica as stationary phase, particularly completely demineralized. The crude product dissolved in an aqueous acid medium is adsorbed at the head of the column; there then follows a desalting step (H$_2$O—H$^+$) before eluting the product by using a CH$_3$CN gradient in H$_2$O/H+. The eluant is fractionated. The fractions containing the product (orange yellow colored fractions) are analysed by HPLC. Those containing the product with a purity higher than 98% are collected and freeze-dried. A bright orange-yellow powder is obtained. The trifluoroacetate counter anion is then changed into a hydrochloride by adding to an aqueous solution of the trifluoroacetate salt an amount of aqueous HCl corresponding approximately to two acid equivalents calculated with respect to the weight of trifluoroacetate salt to be exchanged. The solution obtained (pH 2.8–3) is freeze-dried protected from light (two lyophilisations). The product obtained is in the form of a very hygroscopic bright orange powder. Even stocked under an inert atmosphere (argon), the product deteriorates fairly rapidly in the course of time. It also shows a limited stability in solution: physiological medium or aqueous solution at 0° C. and protected from light.

The quinoleic nucleus is a particularly sensitive target for any oxidation reaction. The latter explains partly the instability observed. For the purpose of inhibiting these oxidation reactions, the aqueous solution containing the trifluoroacetate salt was treated with sodium bisulfite (0.1%).

The relative proportion CH$_3$CN—H$_2$O/H$^+$ varies according to the nature and the number of amino acids bonded to the primaquine.

Synthesis of N-1-L-glutamyl, N-4 (6-methoxy-8-quinolinyl) penta-1,4-diamine

To 5.9 mmoles of N-tBoc-glutamic, dissolved in 10 ml of diglyme, kept at 0° C., were added 0.61 g (5.3 mmoles) of N-hydroxysuccinimide and 1.09 g (5.3 mmoles) of dicyclohexylcarbodiimide. After 4 hours of reaction, 1.37 g (5.3 mmoles) of primaquine base was added. The latter was released from the primaquine diphosphate by the action of a 25% ammonia solution. After 17 hours, the dicyclohexylurea was filtered off and the solvent driven off under vacuum. The brown oil obtained was dissolved in CH$_2$Cl$_2$ and washed with water. The organic phase was dried on sodium sulfate, filtered and evaporated. The product was purified on silicagel using as eluants a dichloromethane-methanol mixture. The pure fractions were collected and the eluant evaporated resulting in 1.5 g of a more or less crystalline product which was fairly hygroscopic.

The product obtained previously was dissolved in 15 ml of a 1:1 mixture of dichloromethane and trifluoroacetic acid. The mixture was stirred for 30 minutes at room temperature. The solvents were evaporated under vacuum and the residue was taken up again in water and washed several times with diisopropylether.

If necessary, the product was purified by reverse phase chromatography (Merck lobar 8) by using as an eluant a mixture of 25% of acetonitrile in water containing 1% of trifluoroacetic acid. The pure fractions (HPLC) were collected, the acetonitrile driven off under vacuum. After 2 lyophilisation cycles, 1.6 g (80%) of a hygroscopic bright orange powder was obtained.

(B) MICROSPHERES:

The microspheres were prepared by the operational method presented in Example 1. The granulometric distribution of 3 preparations is shown in Table 4. As in the case of primaquine diphosphate, a large proportion of injectable microspheres was obtained.

TABLE 4

Granulometric distribution (%) of three preparations of (DL) polylactide microspheres containing L-glutamyl primaquine.

| Sample | Diameter of the microparticles (μm) | | | | | |
|---|---|---|---|---|---|---|
| | 70-100 | 100-160 | 160-200 | 200-250 | 250-315 | >315 |
| PH 52A | 1.1 | 14.8 | 31.9 | 43.2 | 8.4 | 0.5 |
| PH 52B | 1.3 | 18.8 | 19.8 | 20.6 | 28.9 | 10.6 |
| PH 52C | 0.5 | 5.7 | 16.4 | 49.6 | 26.4 | 1.3 |

We claim:

1. Microparticles consisting of microspheres constituted by a polylactide polymer matrix, within which is distributed an active principle which is primaquine, one of its derivatives of the formula

PQ—X in which,
PQ represents primaquine,
X represents an amino acid or a peptide of 2 to 4 amino acids,
the linkage PQ—X being a peptide covalent linkage between the free amine group of PQ and the carboxylic group of X,
or conjugates of PQ or PQ—X with a hepatotropic vector, or one of their pharmaceutically acceptable salts.

2. Microparticles according to claim 1, wherein the molecular weight of the polymer is between 10,000 and 200,000.

3. Microparticles according to claim 1, wherein the ratio by weight active principle/polymer is from 1 to 50%.

4. Microparticles according to claim 1, with a dimension between 1 and 250 μm.

5. Pharmaceutical composition, which contains microparticles according to claim 1.

6. Composition according to claim 5, said composition being injectable.

7. Process for the preparation of microparticles, according to claim 1, said process comprising:
dissolving the polymer in a volatile solvent,
adding to this solution, the active principle and after evaporation, recovering the microparticles by centrifugation and filtration.

8. Process according to claim 7, wherein the primaquine or one of its derivatives or conjugates, or one of their pharmaceutically acceptable salts is incorporated in polylactide, the solvent being acetone and the dispersing medium being a mineral oil, such as paraffin, the substance regulating the size of the particles being a non-ionic surface-active agent.

9. Process according to claim 8, wherein the polylactide is in (DL) form.

10. Process according to claim 7, wherein the ratio by weight of polymer/solvent is from 10 to 30%, and the ratio by weight of active principle/polymer is from 1 to 50%.

11. Process according to claim 7, wherein the dispersion of the active principle in the acetone is done by the use of ultrasound.

12. Process according to claim 8, comprising using as non-ionic detergent, a sorbitan ester preferably in a concentration comprised between 1 and 10%.

13. Process according to claim 8, wherein the sorbitan ester is sorbitan monooleate used in the proportion of 5% by weight with respect to the acetone.

14. Microparticles according to claim 1, wherein the polylactide polymer matrix is in (DL) form.

15. Microparticles according to claim 1, wherein the molecular weight of the polymer is between 50,000 and 100,000.

16. Microparticles according to claim 1, wherein the ratio by weight active principle/polymer is from 15 to 25%.

17. Microparticles according to claim 1, with a dimension between 100 and 200 μm.

18. Process according to claim 7, further comprising the step of adding a substance regulating the size of the microparticles to the solution of the polymer in the volatile solvent, before evaporation.

19. Process according to claim 10, wherein the ratio by weight of polymer/solvent is from 15 to 20%.

20. Process according to claim 10, wherein the ratio by weight of active principle/polymer is from 15 to 25%.

* * * * *